US005488948A

United States Patent [19]

Dubruille et al.

[11] Patent Number: 5,488,948

[45] Date of Patent: Feb. 6, 1996

[54] FAST DONNING RESPIRATORY PROTECTION EQUIPMENT

[75] Inventors: Alain Dubruille, Rambouillet; Patrick Morvan, Saint-Laurent-Les-Gâtines, both of France

[73] Assignee: Intertechnique, Plaisir, France

[21] Appl. No.: 305,924

[22] Filed: Sep. 16, 1994

[30] Foreign Application Priority Data

Sep. 23, 1993 [FR] France .................................... 93 11342

[51] Int. Cl.[6] .......................... A61M 16/00; A62B 18/08

[52] U.S. Cl. ................................ 128/207.11; 128/206.21; 128/206.27; 2/6.1; 2/422

[58] Field of Search ............................ 2/9, 6.1, 6.2, 413, 2/422, 424; 128/201.22, 201.23, 201.24, 206.26, 207.11, 206.24, 206.27, 206.21

[56] References Cited

U.S. PATENT DOCUMENTS

| | | | |
|---|---|---|---|
| 2,312,630 | 3/1943 | Dauster | 128/207.11 |
| 2,444,417 | 7/1948 | Bierman | 128/206.24 |
| 2,827,900 | 3/1958 | Marietta | 128/207.11 |
| 3,330,273 | 7/1967 | Bennett | 128/206.26 |
| 3,599,636 | 8/1971 | Gutman | 128/146.7 |
| 4,437,462 | 3/1984 | Piljay et al. | 128/207.11 |
| 4,915,106 | 4/1990 | Aulgur et al. | 128/207.11 |
| 5,179,735 | 1/1993 | Thomanek | 2/422 |
| 5,291,880 | 3/1994 | Almovist et al. | 128/201.22 |

FOREIGN PATENT DOCUMENTS

| | | |
|---|---|---|
| 0288391 | 4/1988 | European Pat. Off. . |
| 0471264 | 8/1991 | European Pat. Off. . |
| 8907961 | 9/1989 | WIPO . |

OTHER PUBLICATIONS

"Eros Quick Donning Mask Brochure" by Scott Avation Dt. 7/80 Maintained in files.

*Primary Examiner*—Edgar S. Burr
*Assistant Examiner*—V. Srivastava
*Attorney, Agent, or Firm*—Larson and Taylor

[57] ABSTRACT

The fast donning breathing apparatus for use by a crew member comprises a mask provided with a regulator for connection to a source of pressurized breathable gas and a harness having. The harness has a stretchable strap having ends connected to the mask and including an element which is optionably inflatable by the pressurized breathable gas to extend the strap up to a size which is sufficient to permit fitting of the harness on the head and deflatable to enable the strap to tighten, to bias the mask onto the face and to hold the mask in position. The harness also has a flexible hardly extensible additional strap. A fastener enables to adjust the length of the additional strap and permits direct manual tightening by a user.

7 Claims, 3 Drawing Sheets

FAST DONNING RESPIRATORY PROTECTION EQUIPMENT

BACKGROUND OF THE INVENTION

The invention relates to respiratory protection apparatuses comprising a breathing mask, a harness for fast donning, and sometimes goggles for protection against smoke, which may be integral with the mask or not.

Fast donning safety apparatuses for use by flight crew members of passenger planes are known which comprise a breathing mask with a regulator arranged for connection to a source of pressurized breathable gas (typically pressurized oxygen) and a harness having at least one extensible strap whose ends are connected to the mask and which has an element which is inflatable by the pressurized gas for extending a strap until it has a sufficient size for enabling the user to quickly don the harness over the head and deflatable to permit the strap to tighten, to urge the mask against the face and to maintain the mask on the face. The demand regulator is typically with air dilution. The mask may be designed for being fed with pressurized gas (which requires that the harness is able to exert a tension on the mask which is sufficient for air-tight contact of the mask with the face, in spite of the overpressure) or not.

Existing apparatuses of the above-defined type are hardly usable by crew members which wear a helmet and are located in a pressurized cabin designed for them to work, even at the maximum flight altitude of the plane, without a respiratory mask, although fast donning of the mask is required if depressurization occurs. That situation is that of crew members in military planes other than fighters (transport, patrol, reconnaissance, service, flight refueling planes for instance) which are often above a flight level which involves depressurization risks and/or which may be faced with invasion of smoke or toxic gas.

Overdimensizing an inflatable harness of an apparatus of the presently available type, to an extent sufficient for easy donning over a helmet, is not satisfactory. The force that a harness would have to exert for air tightness against the face (which is required under the most unfavorable depressurization conditions) would cause an unacceptable lack of comfort when such a situation is not present. The amount of tension exerted by an inflatable harness, except if so high that wearing the mask becomes unacceptable with a helmet during long periods, is not sufficient for retaining the mask on the face under exceptional conditions, such as in-flight ejection of crew members.

SUMMARY OF THE INVENTION

It is an object of the invention to provide an equipment for respiratory protection, particularly against hypoxia, which is capable of being donned over a helmet in a short time and which may be worn for long periods without sacrificing safety.

For that purpose, there is provided an equipment wherein the harness further comprises a flexible additional strap, which is inextensible or hardly extensible, provided with a fastener for direct manual tightening. An additional strap may be considered as hardly extensible if its length does not vary by more than some per cent responsive to a tractive force exerted thereon.

The additional strap may be constituted by a single band or belt consisting of two parts which are connected by a fastener which is continuously in place and which can be tightened by manually pulling a projecting free end. For avoiding that the presence of the additional strap impedes fast donning the harness on the helmet and/or fast donning over the head, the additional strap is advantageously connected to the strap or straps which stretch when pressurized, for it to follow the movement of the extensible strap or straps.

Particularly, when the harness comprises two inflatable straps constituting a V from each point of connection on the mask, as described for instance in document EP-A-0,288,391, the additional strap may be located between the two inflatable straps and may be connected to the latter by bands distributed around the head.

Supplemental elements may be provided for more effective fastening of the mask under exceptional circumstances. For instance, a chin piece may be provided and may be adjustable or not. A higher band for contact on the helmet, for avoiding downward displacement of the mask (for instance in case of bail-out) may be provided and it may be fitted or not with means for adjusting the degree of tightening thereof.

Last, it is possible to design the equipment for enabling a crew member having the equipment to temporarily shorten the harness before a mission, if the whole mission or part of it is without a helmet.

The mask may be oro-nasal, typically with such a shape that goggles or a transparent shield may be adapted thereto for protecting the eyes. The mask may as well be a full mask with goggles fast with the face cover.

The invention will be better understood from the following description of particular embodiments, given by way of non-limiting examples. The description refers to the accompanying drawings.

DESCRIPTION OF PARTICULAR EMBODIMENTS

Figure 1:
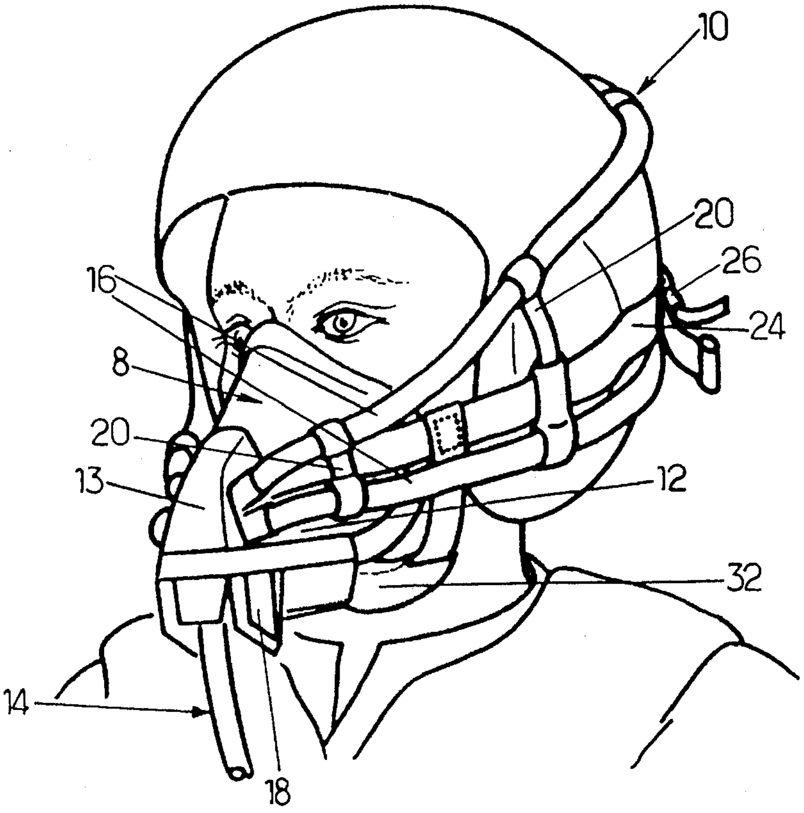
FIG. 1 is a isometric view illustrating the external aspect of a protection equipment according to a first embodiment of the invention.

Referring to FIG. 1, an emergency breathing apparatus is illustrated in its position of use, when on the head of a user. It may be considered as having a mask 8 and a harness 10. As shown, the mask has an oro-nasal face piece secured to a demand regulator 13 and to a rigid connecting block 12. The connecting block has a nozzle for connection with a flexible hose 14 apt to be connected to a source of pressurized breathable gas (typically pressurized oxygen). As represented by way of example, the harness comprises two straps 16 each consisting of an inner tube of resilient material in an inextensible covering sheath which limits the degree of extension of the inner tube. The length of the inner tubes when free is such that they urge the face piece onto the face with a force sufficient for achieving the required degree of sealing, even when a breathing overpressure prevails in the mask.

Depending upon the use for which the equipment is designed, the regulator will or will not cause dilution with air drawn from the cabin and will be with or without pressurization.

The regulator is connected to the flexible feed hose 14 by the connecting block 12. The block carries means for manual control of inflation of the straps 16. Such means may consist for instance of a valve unit arranged to be controlled by manually squeezing two levers 18 carried by the connecting block 12, one of which is pivotable.

The valve is arranged for communicating an inner volume of the connecting block 12 and the straps 16 with atmosphere when released. Then the straps can retract and urge the mask against the wearer's face. When on the other hand the valve is open, it delivers pressurized gas from the flexible feed hose 14 into the volume and causes the straps to stretch sufficiently for enabling fast donning. For the straps to have a satisfactory contact with the rear of the head, when retracted, they are preferably connected by cords 20 which limit their degree of spacing.

The arrangement which has been described up to now is known. A description may for instance be found in document EP-A-0,288,391. However, the length of the covering sheaths should be such that the straps authorize passing the harness over a helmet of any size.

Figure 2:
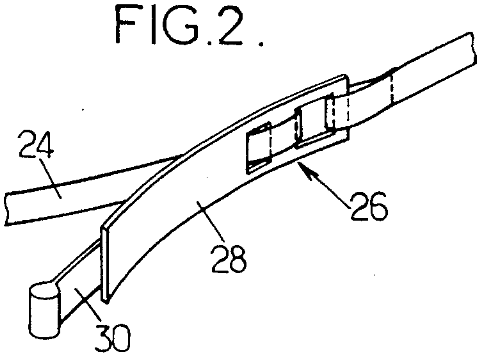
FIG. 2 illustrates a possible construction of a fast tightening fastener which may be carried by the single additional strap of the equipment of FIG. 1.

The harness further comprises at least one additional flexible strap 24 which is not resiliently stretchable or is hardly stretchable, but is apt to be manually tightened on the helmet for urging the mask more tightly onto the face. As shown in FIG. 1, the strap 24 is in three sections connected by two fasteners 26 each placed on one side of the head and each easily adjustable by the wearer of the mask for tightening the additional strap. The fasteners may for instance have a construction schematically illustrated in FIG. 2. Then the fastener comprises an elongated metal buckle 28 secured to an end of one of the sections of the additional strap 24. The end part of another section constitutes a loop which slides around a transverse bar of buckle 28 and has a free end 30. Pulling the free end tightens the additional strap 24.

For that strap to have a proper location when tightened, it advantageously passes through the cords 20 which maintain it between the two inflatable straps 16.

As illustrated in FIG. 1, the harness further has a chin piece 32 which may be adjustable or not, and which prevents the mask from sliding toward the eyes.

Except during the periods when the harness should be tightened on the helmet due to a risk of being torn away or lifted, the operation is the same as that of a fast donning equipment of known type, except that the additional strap 24, typically of flexible fabric, should be sufficiently long for not interfering with the helmet. In a situation which requires tight application and avoidance of upward movement, the wearer of the equipment has just to pull the free ends 30 until the required tension is obtained.

Figure 3:
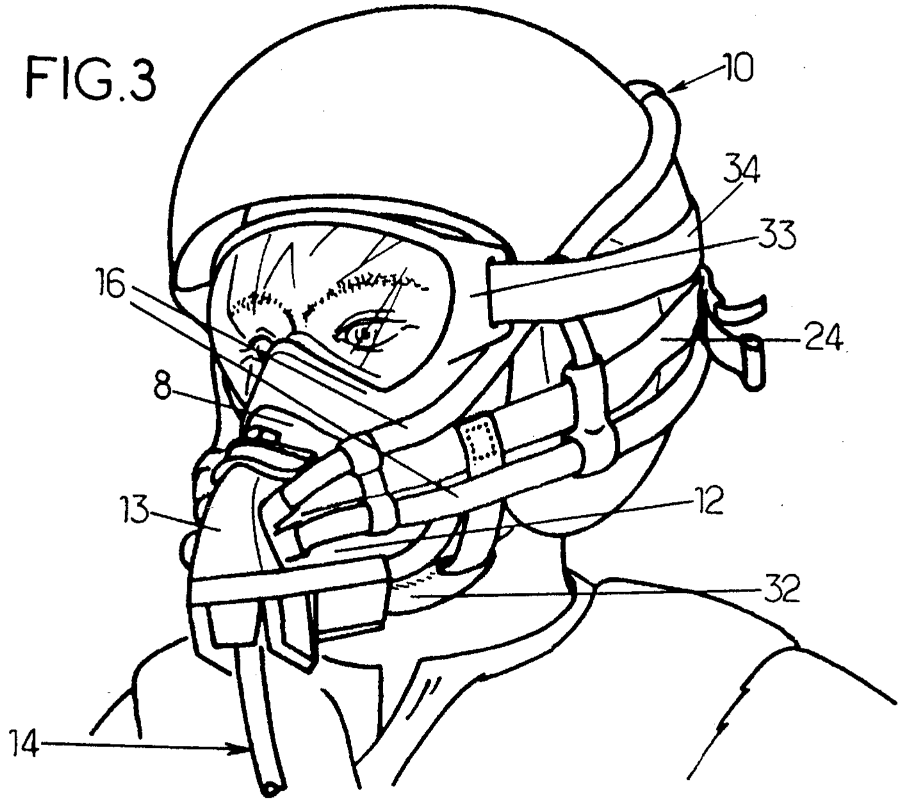
FIGS. 3, 4 and 5, similar to FIG. 1, illustrate modified embodiments.

The modified embodiment illustrated in FIG. 3 (where the components corresponding to those of FIG. 1 are designated by the same reference numeral) comprises goggles 32 for protection against smoke. The goggles have their own retaining element 34, which can be tightened on the helmet independently from the harness.

Figure 4:
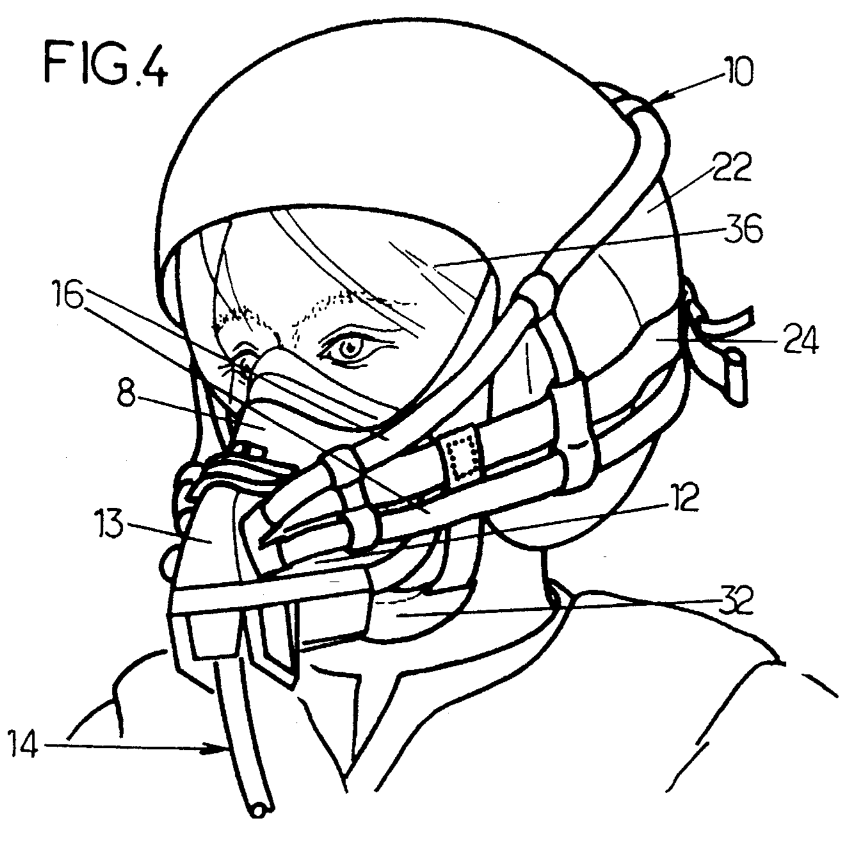

Rather than goggles, the embodiment of FIG. 4 as a transparent eye-shield 36 which is integral with the mask, according to an arrangement which is comparable to that described in U.S. Pat. No. Des. 304,384.

Figure 5:
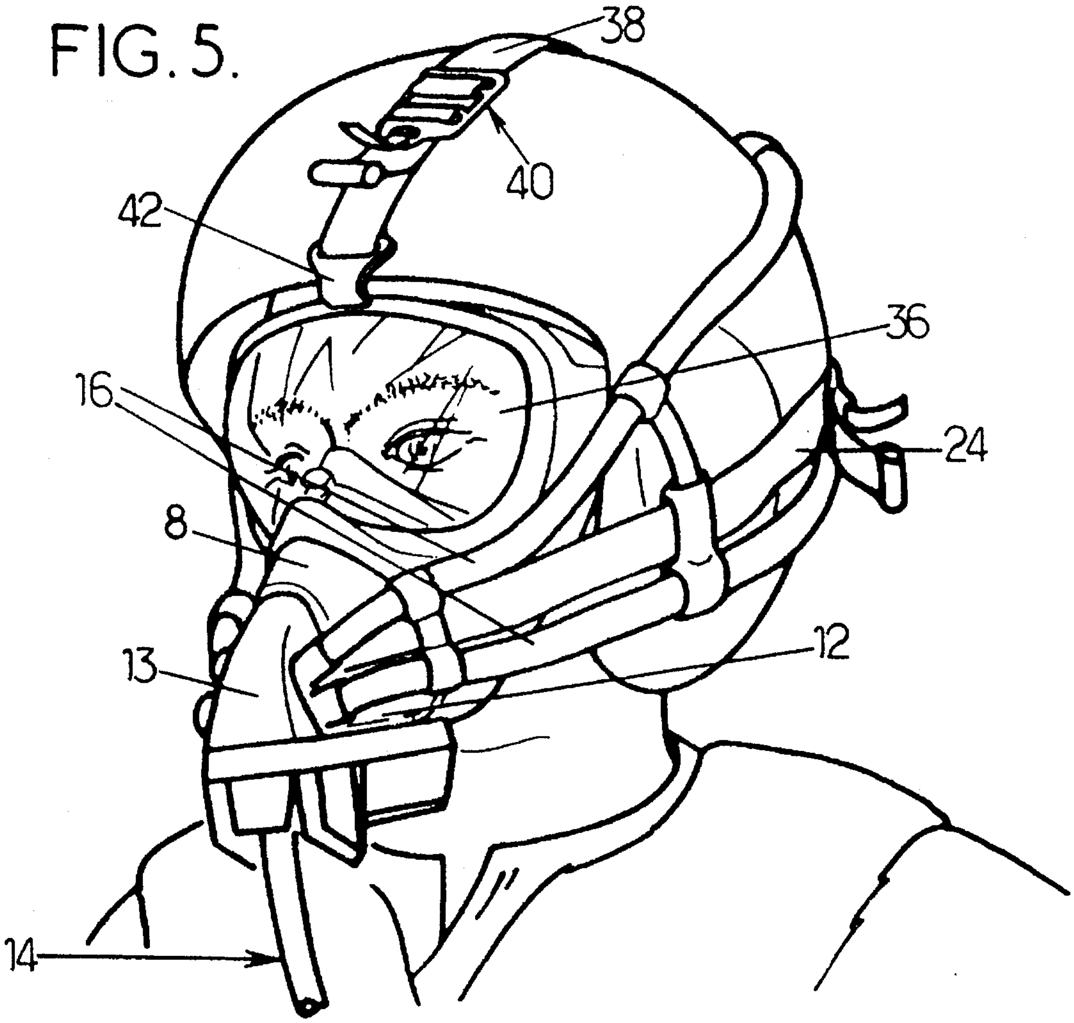

Last, the embodiment of FIG. 5 differs from the preceding one in that it comprises not only a lateral additional strap 24, but also a higher strap or band 38. Strap 38, as strap 24, has a fastener 40 which makes it possible to tighten it if need arises. As illustrated on FIG. 5, the higher strap 38 has an end hook 42 which can engage the edge of the helmet and it may be connected to strap 24 at its other end. As strap 24, the higher strap 38 may be lengthened before storage, for not impeding fast doning. The higher strap may also be located transversely and interconnect the two sides of the higher strap 16.

During certain missions, the crew members may have to wear a helmet temporarily, while incidents may render it necessary to don the respiratory equipment in an emergency. Then it is possible to provide the harness with a tension fastening element which is easily removable and which temporarily shortens one at least of the inflatable straps.

Figure 6:
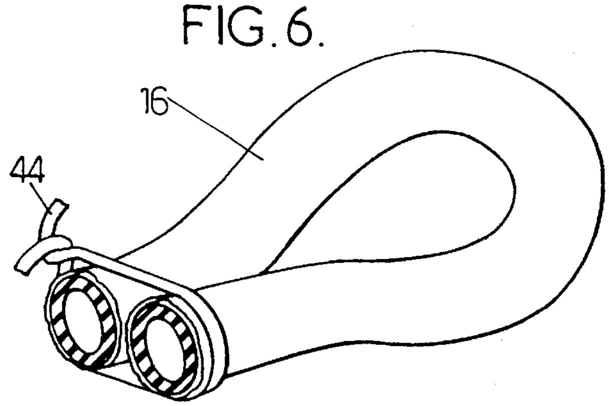
FIGS. 6 and 7 illustrate possible constructions of a supplemental element making it possible to temporarily shorten the harness, for a mission which does not require wearing a helmet.

Referring to FIG. 6, a possible construction of such a tension fastener is shown. It consists of a clamp made of metal wire (spring steel for instance) which is apt to retain the base of a loop formed on one of the inflatable straps 16. Before a mission which does not require permanently wearing the helmet, the user has just to locate the clamp 44 and may easily and rapidly release it by separating the two ends, while the mid portion may be secured to the strap.

The clamp 44 may have a number of shapes which differ from that described as an example.

Figure 7:
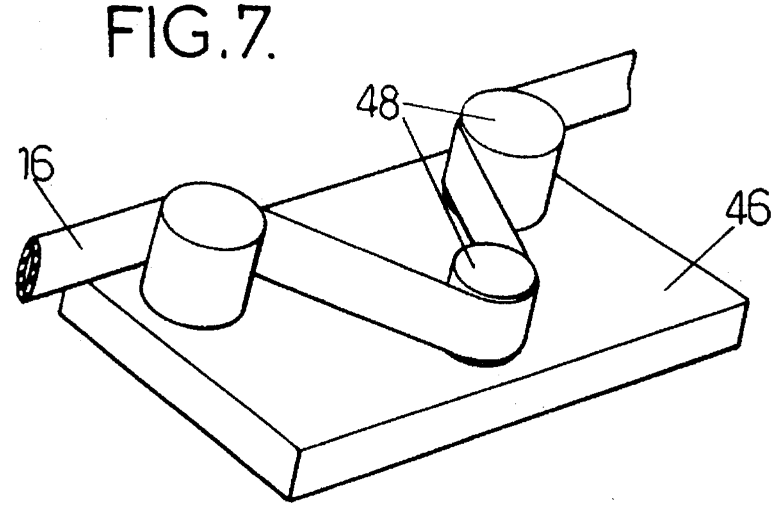

Another possible construction of the clamp is represented on FIG. 7. The clamp then comprises a plate 46 and pins 48 around which at least one of the harness strap is passed for increasing the tension and the degree of tightening on the head.

We claim:

1. Fast donning breathing apparatus, comprising:

a mask provided with a regulator arranged for connection to a source of pressurized breathable gas; and a harness having:

two stretchable straps forming Vs from common points of attachment on the mask and each including an inflatable element, means connectable to a source of pressurized breathable gas and manually controllable to admit a pressurized breathable gas to the inflatable elements to extend said stretchable straps up to a large size and to discharge said pressurized breathable gas from said inflatable elements to decrease the size of said stretchable strap and to enable the straps to tighten and to bias the mask onto a face of a wearer, a flexible hardly extensible additional strap having a fastener arranged for direct manual tightening by the wearer, said additional strap being located between said two stretchable straps, and a plurality of bands connecting said additional strap to said stretchable straps at intervals.

2. Apparatus according to claim 1, wherein said flexible additional strap comprises at least two sections connected by said fastener which is so constructed as to be tightened upon a manual pulling on a free end of the additional strap.

3. Apparatus according to claim 2, wherein said additional strap is locally connected to at least one said stretchable strap, whereby said additional strap follows movements of said one of said stretchable straps

4. Apparatus according to claim 1, further comprising a higher band for contact with a wearer's helmet, connected to said additional strap and provided with end means for engaging an edge of said helmet.

5. Apparatus according to claim 4, wherein said higher band has fastener means for manual adjustment of the length thereof.

6. Fast donning breathing apparatus for use by a wearer with and without a helmet, comprising:

a mask provided with a regulator arranged for connection to a source of pressurized breathable gas;

and a harness having:

a pair of stretchable straps having ends connected to said mask at connecting points to form Vs from said connecting points and including an element which is inflatable by a pressurized breathable gas to extend the strap up to a size which is sufficient to permit fitting of the harness over the helmet and is deflatable to enable the strap to tighten and to tightly seal the mask onto a wearer's face when located around the helmet, cord means interconnecting said stretchable straps, and a flexible additional strap of hardly extensible material having a fastener arranged for direct manual tightening by the wearer of the equipment, said additional strap being located between the two stretchable straps and passing through said cord means.

7. Apparatus according to claim 6, further comprising tensioning means located on at least one of the stretchable straps and manually actuatable to shorten or lengthen said one of the stretchable straps by a predetermined amount.

* * * * *